(12) United States Patent
Kandori et al.

(10) Patent No.: US 9,233,395 B2
(45) Date of Patent: Jan. 12, 2016

(54) CONTROL APPARATUS AND METHOD FOR ELECTROMECHANICAL TRANSDUCER DEVICE, AND MEASUREMENT SYSTEM

(75) Inventors: Atsushi Kandori, Ebina (JP); Masao Majima, Isehara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 591 days.

(21) Appl. No.: 13/508,437

(22) PCT Filed: Nov. 11, 2010

(86) PCT No.: PCT/JP2010/070523
§ 371 (c)(1),
(2), (4) Date: May 7, 2012

(87) PCT Pub. No.: WO2011/062208
PCT Pub. Date: May 26, 2011

(65) Prior Publication Data
US 2012/0227498 A1    Sep. 13, 2012

(30) Foreign Application Priority Data

Nov. 17, 2009    (JP) .................................. 2009-262068

(51) Int. Cl.
*G01N 29/36* (2006.01)
*B06B 1/02* (2006.01)
(Continued)

(52) U.S. Cl.
CPC .......... *B06B 1/0292* (2013.01); *G01N 21/1702* (2013.01); *G01N 29/2418* (2013.01)

(58) Field of Classification Search
CPC .................................................... G01N 29/36
USPC ............ 73/570, 584, 627; 600/407, 437, 439, 600/443, 459, 463, 471, 547
See application file for complete search history.

(56) References Cited

U.S. PATENT DOCUMENTS 8,214,010 B2 *  7/2012  Courtney et al. ............. 600/407
8,712,506 B2 *  4/2014  Courtney et al. ............. 600/478
(Continued)

FOREIGN PATENT DOCUMENTS

| | | |
|---|---|---|
| CN | 2425716 Y | 4/2001 |
| CN | 101152646 S | 4/2008 |

(Continued)

OTHER PUBLICATIONS

Srikant Vaithilingam et al.; 3-D Photoacoustic Imaging Using a 2-D CMUT Array; IEEE Transactions on Ultrasonics, Ferroelectrics, and Frequency Control, vol. 56, No. 11, Nov. 2009; pp. 2411-2419.

*Primary Examiner* — Hezron E Williams
*Assistant Examiner* — Hoang Nguyen
(74) *Attorney, Agent, or Firm* — Canon USA, Inc. IP Division

(57) ABSTRACT

There is a case in which a generated acoustic wave is decreased owing to the attenuation of light, whereby a desired output is not obtained from an electromechanical transducer device that receives the acoustic wave. The control apparatus for controlling an electromechanical transducer device of the present invention includes: a conversion unit that converts a current output from a first electrode of the electromechanical transducer device to a voltage; a DC voltage applying unit that applies a DC voltage to a second electrode arranged with a gap between itself and the first electrode; and a generation unit that generates a control signal which makes at least one of the DC voltage and a conversion ratio for converting the current to the voltage be changed, on the basis of information about an elapsed time from a point in time at which an inspection object was irradiated with light.

21 Claims, 7 Drawing Sheets

(51) Int. Cl.
*G01N 21/17* (2006.01)
*G01N 29/24* (2006.01)

(56) References Cited

U.S. PATENT DOCUMENTS

| | | | |
|---|---|---|---|
| 2005/0007644 A1* | 1/2005 | Onuki et al. | 359/253 |
| 2007/0016020 A1* | 1/2007 | Oshiki et al. | 600/437 |
| 2007/0287912 A1* | 12/2007 | Khuri-Yakub et al. | 600/439 |
| 2009/0005685 A1* | 1/2009 | Nagae et al. | 600/459 |
| 2009/0301199 A1* | 12/2009 | Azuma et al. | 73/603 |

FOREIGN PATENT DOCUMENTS

| | | |
|---|---|---|
| CN | 101170281 A | 4/2008 |
| JP | 02-289236 A | 11/1990 |
| JP | 2006-122344 A | 5/2006 |
| JP | 2009-031268 A | 2/2009 |
| JP | 2010-516304 A | 5/2010 |
| WO | 2005/032374 A | 4/2005 |
| WO | 2006/041114 A1 | 4/2006 |
| WO | 2009/076427 A1 | 6/2009 |

\* cited by examiner

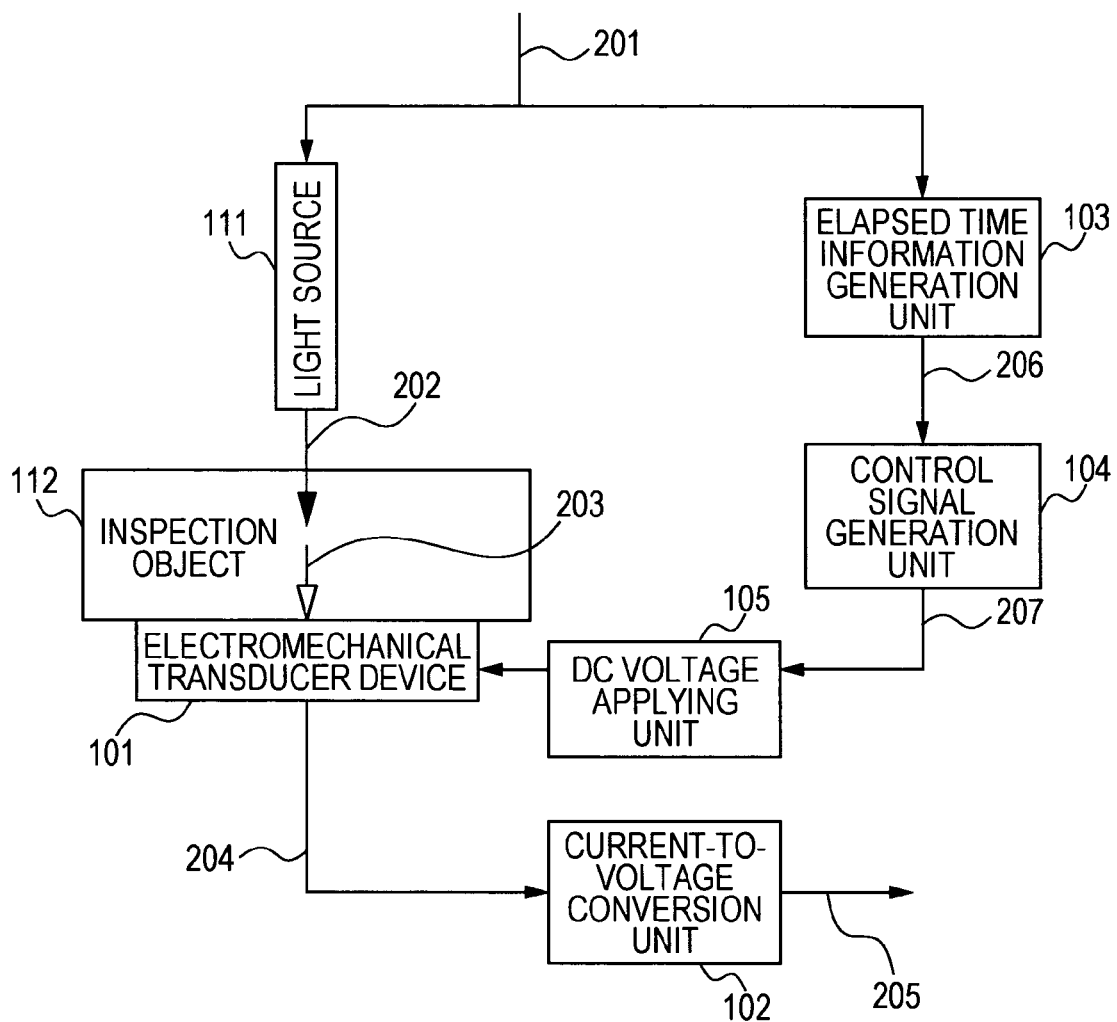

CONTROL APPARATUS AND METHOD FOR ELECTROMECHANICAL TRANSDUCER DEVICE, AND MEASUREMENT SYSTEM

TECHNICAL FIELD

The present invention relates to control apparatuses and methods for driving of electromechanical transducer devices, and measurement systems. In particular, the present invention relates to a control apparatus and method for a capacitive electromechanical transducer device that receives acoustic waves generated due to the photoacoustic effect, and a measurement system including the electromechanical transducer device.

BACKGROUND ART

There exists a measurement system in which an inspection object is irradiated with light to make a measurement object in the inspection object generate acoustic waves (typically, ultrasonic waves) due to the photoacoustic effect, and the generated photoacoustic waves are received using an electromechanical transducer device. An exemplary existing electromechanical transducer device is a capacitive micromachined ultrasonic transducer (CMUT) device, which is a capacitive electromechanical transducer device that has an advantage of having a wide acoustic-wave receiver frequency band. CMUT devices are produced using a MEMS process, which is an application technology of a semiconductor process. A method of using a CMUT device as an electromechanical transducer device which is used in a measurement system based on the photoacoustic effect is proposed in Patent Literature PTL 1.

CITATION LIST

Patent Literature

PTL 1 U.S. Patent Application Publication No. 2007/0287912 A1

SUMMARY OF INVENTION

In a measurement system based on the photoacoustic effect, an inspection object is made to generate a photoacoustic wave based on the photoacoustic effect, by irradiating the inspection object with light, which is generated by making a light source periodically perform illumination in the form of pulses having a predetermined width. However, when an inspection object such as a living body is to be inspected, light used for irradiation is attenuated exponentially in accordance with a distance travelled through the inspection object. Hence, the intensity (sound pressure) of an acoustic wave generated from a measurement object (such as a tumor) depends on the depth at which the measurement object exists. When the generated sound pressure is small, the sound pressure received by an electromechanical transducer device may be below the receiver sensitivity (minimum sound pressure which can be received) of the electromechanical transducer device. One way to avoid this is to set the receiver sensitivity to be always at a high level. However, in this case, a detected signal having a high sound pressure is saturated and cannot be output. Hence, the present invention provides a control apparatus and method for a capacitive electromechanical transducer device, taking into consideration light attenuation in an inspection object.

The present invention provides a control apparatus that controls an electromechanical transducer device having an element that includes a first electrode and a second electrode arranged with a gap therebetween, and that outputs a current from the first electrode due to receiving an acoustic wave generated by light with which an inspection object is irradiated in a state where a DC voltage is applied to the second electrode, and the control apparatus includes: a conversion unit configured to convert the current output from the first electrode to a voltage; a DC voltage applying unit configured to apply a DC voltage to the second electrode; and a generation unit configure to generate a control signal which makes at least one of the DC voltage and a conversion ratio for converting the current to the voltage be changed, on the basis of elapsed time information about an elapsed time from a point in time at which the inspection object was irradiated with the light.

The present invention also provides a control method of controlling an electromechanical transducer device having an element that includes a first electrode and a second electrode arranged with a gap between the first and second electrodes, and that outputs a current from the first electrode due to receiving an acoustic wave generated by light with which an inspection object is irradiated in a state where a DC voltage is applied to the second electrode, and the method comprises: converting the current output from the first electrode to a voltage; applying a DC voltage to the second electrode; and generating a control signal which makes at least one of the DC voltage and a conversion ratio for converting the current to the voltage be changed, on the basis of information about an elapsed time from a point in time at which the inspection object was irradiated with the light.

Since a capacitive electromechanical transducer device is controlled taking into consideration the attenuation of light in an inspection object, the effect of a decrease in the electromechanical transducer device output is decreased.

BRIEF DESCRIPTION OF DRAWINGS

FIG. 1 is a schematic diagram illustrating a measurement system according to a first embodiment.

DESCRIPTION OF EMBODIMENTS

Figure 2A:
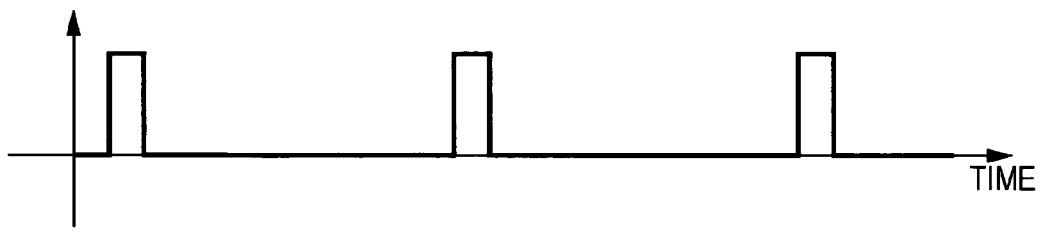
FIGS. 2A to 2D are schematic diagrams illustrating the generation and attenuation of light.

In the present invention, at least one of the following two methods is employed to deal with the effect of a decrease in the output of an electromechanical transducer device, caused by the attenuation of light. The first method is to increase the required receiver sensitivity for an acoustic wave in accordance with the attenuation of light, thereby increasing the output of the electromagnetic transducer device. An embodiment using this method is described as a first embodiment. The second method is to increase a conversion coefficient for converting a current output from the electromechanical transducer device to a voltage in accordance with the attenuation of light, without adjusting the output of the electromechanical transducer device. An embodiment using this method is described as a second embodiment. Thus, both of the embodiments can reduce an effect caused by a decrease in the strength of a signal, in accordance with the attenuation of light, which is output to an external apparatus for generating image data.

Hereinafter, the present invention is described in details with reference to the attached drawings. Note that, in the present invention, acoustic waves include what are called sound waves, ultrasonic waves, and photoacoustic waves, and refer to elastic waves generated within an inspection object by irradiating the inspection object with light (electromagnetic waves) such as near infrared rays.

First Embodiment

The present embodiment is characterized in that receiver sensitivity is changed by changing a drive voltage (DC voltage) applied to a capacitive electromechanical transducer device in accordance with a time elapsed from a point at which an inspection object was irradiated with light.

FIG. 1 illustrates a schematic diagram of a measurement system including a control apparatus for an electromechanical transducer device which can be applied to the present embodiment. In this measurement system, which utilizes the photoacoustic effect, an inspection object 112 is irradiated with light 202 (pulsed light) by making a light source 111 generate the light 202 in response to a light emission instruction signal 201. An acoustic wave is generated from a measurement object (acoustic wave generating source) within the inspection object 112 owing to irradiation with the light 202. This acoustic wave is received by an electromechanical transducer device 101, which is an acoustic wave receiver. The electromechanical transducer device 101 converts vibration caused by the received acoustic wave to an electric signal (current) 204 and outputs the current 204 to a current-to-voltage conversion unit 102. The current-to-voltage conversion unit 102 converts the input current 204 to a voltage 205, and outputs the voltage 205 to the input unit (such as an AD converter or phasing adder) of an external apparatus (not illustrated) for generating image data or the like. Examples which can be used as the current-to-voltage conversion unit 102 include a transimpedance circuit. An elapsed time information generation unit 103 generates information about an elapsed time from an ON signal (a point in time corresponding to the center of the pulse width as a reference, for example), included in the light emission instruction signal 201, as elapsed time information 206, and outputs the elapsed time information 206 to a control signal generation unit 104. The control signal generation unit 104 generates a control signal 207 on the basis of the elapsed time information 206, and outputs the control signal 207 to a DC voltage applying unit 105 which applies a drive voltage (DC voltage) to the electromechanical transducer device 101. A control apparatus that controls the electromechanical transducer device 101 according to the present embodiment includes at least the control signal generation unit 104, the DC voltage applying unit 105, and the current-to-voltage conversion unit 102. The elapsed time information generation unit 103 may be included in the control apparatus or may be included in a separate apparatus (such as the drive controller for the light source 111). Here, the current-to-voltage conversion unit 102, the elapsed time information generation unit 103, the control signal generation unit 104, and the DC voltage applying unit 105 may be realized using, for example, a PC or embedded CPU, FPGAs, or analog circuits. These can be integrated in a dedicated control IC chip, so as to be arranged near or integrated with the electromechanical transducer device 101.

Figure 2B:
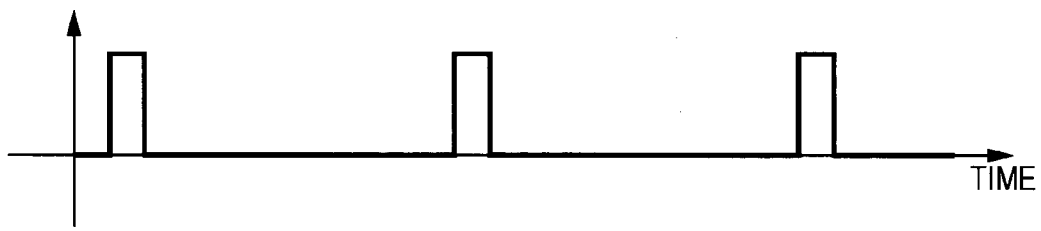
Figure 2C:
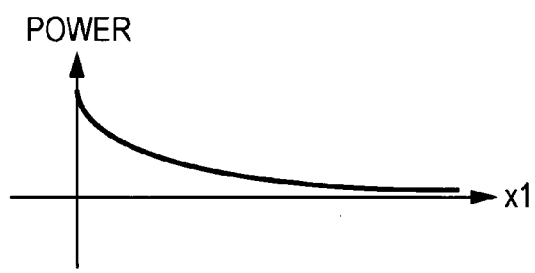
Figure 2D:
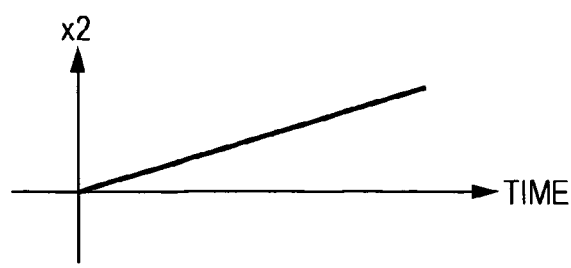

The generation and attenuation of the light 202, on which the present invention is focusing, will now be described with reference to FIGS. 2A to 2D. In FIG. 2A, the horizontal axis shows time and the vertical axis shows the magnitude of a drive signal that drives the light source 111. In FIG. 2B, the horizontal axis shows time, and the vertical axis shows the intensity of light generated from the light source 111. In FIG. 2C, the horizontal axis shows a distance x1 travelled by light through an inspection object, and the vertical axis shows the intensity of the light. In FIG. 2D, the horizontal axis shows time and the vertical axis shows a distance x2 from the electromechanical transducer device 101.

As FIG. 2A illustrates, the light emission instruction signal 201 is a periodical pulse signal, and when the light emission instruction signal 201 is ON, light is generated by the light source 111. The light source 111, in response to the light emission instruction signal 201, periodically emits light (refer to FIG. 2B). The inspection object 112 is irradiated with the light 202 generated by the light source 111. Referring to FIG. 2C, the intensity of the light with which the inspection object 112 is irradiated decreases exponentially in accordance with a distance travelled by the light through the inspection object. In the present invention, the relationship between the distance x1 travelled by the light through the inspection object and the light intensity is called a light attenuation relationship. Since light travels at a very high speed, it can be considered that the light reaches everywhere in the inspection object at the same time as when the light is generated by the light source.

On the other hand, since an acoustic wave generated by the light 202 travels through the inspection object at a fixed low speed, the time spent by the acoustic wave before arriving at the electromechanical transducer device 101 changes in accordance with the distance x2 between the electromechanical transducer device 101 and an acoustic wave generation source (refer to FIG. 2D). Hence, it can be determined how far a location of the acoustic wave generation is from the electromechanical transducer device 101, on the basis of an elapsed time t from the point in time at which the light source 111 generated the light (same as the point in time at which the inspection object was irradiated with light). In other words, the location of an acoustic wave generation source within the inspection object 112 can be determined from the relationships among the elapsed time t from the point in time at which light was generated, the location of the electromechanical transducer device 101, the location of irradiation with the light 202, the location of the inspection object 112, and the like. On the basis of this location of the acoustic wave generation source and the light attenuation relationship, "the relation between an elapsed time from the irradiation with light and the attenuation of the light" is obtained. This relation shows the amount of received light that caused generation of an acoustic wave which arrives after the elapsed time t. This allows determination of the intensity of an acoustic wave (i.e., sound pressure) which arrives at the electromechanical transducer device 101, i.e., the intensity of an acoustic wave which needs to be received. In the present embodiment, in accordance with the attenuation of light, the receiver sensitivity for an acoustic wave is increased by increasing the magnitude of the required output from the electromechanical transducer device 101.

Figure 3:
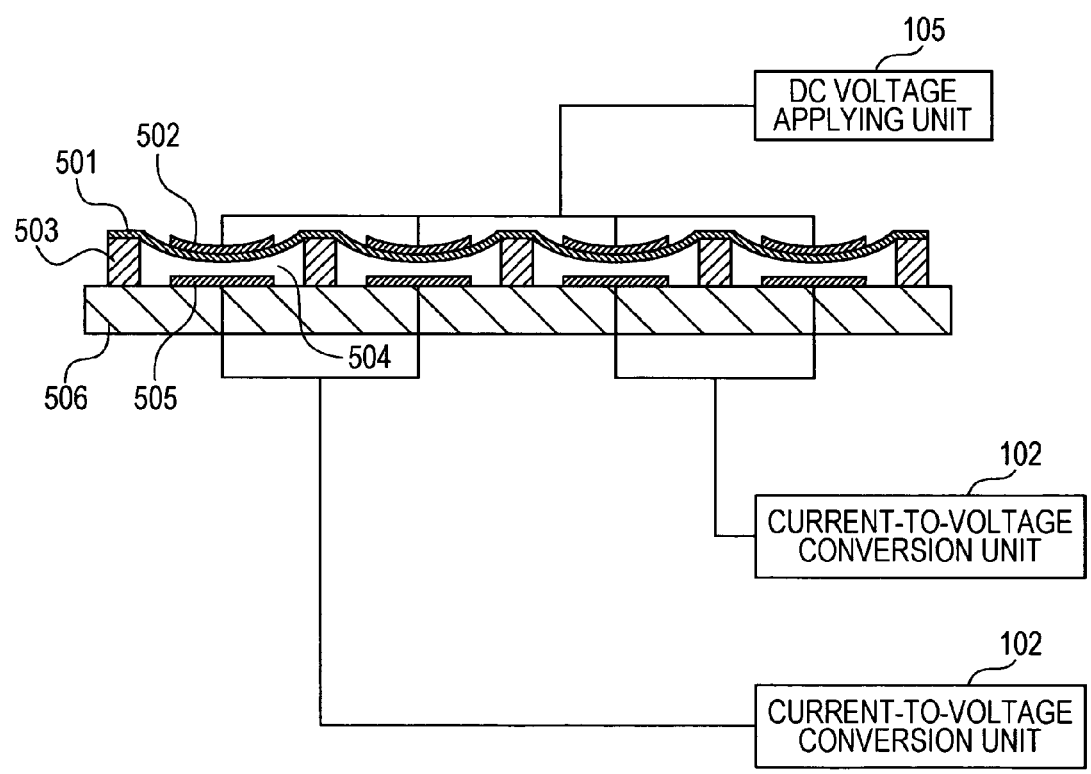
FIG. 3 is a schematic diagram illustrating an electromechanical transducer device to which the present invention can be applied.

Here, the electromechanical transducer device 101 which can be applied to the present invention is described with reference to FIG. 3. FIG. 3 is a schematic diagram illustrating a cross section of the electromechanical transducer device 101, the DC voltage applying unit 105, and the current-to-voltage conversion units 102. Each cell of the capacitive electromechanical transducer device 101 has a lower electrode 505 formed on a substrate 506 thereof and an upper electrode 502 arranged above the lower electrode 505 with a gap 504 (usually several tens of to nine hundred nanometers) therebetween. In the present embodiment, the upper electrode 502 is formed on a vibration diaphragm 501, and the vibration diaphragm 501 is supported by a supporting unit 503 formed on the substrate 506. In the present invention, a component formed of such a pair of electrodes facing each other with the vibration diaphragm 501 and the gap 504 therebetween is called a cell, which is a minimum vibration unit. A configuration in which a plurality of the cells are electrically connected to one another in parallel is called an element. Although two cells constitute one element in FIG. 3, the present invention is not limited to this configuration, and a single cell may constitute one element, or a plurality of cells may be connected to one another in a two-dimensional array. In addition, any number of elements may be provided, and may be arranged in an array. A CMUT device, which is an electromechanical transducer device, usually has about 200 to 4000 elements arranged in a two-dimensional array, where each element (one pixel) includes about 100 to 3000 cells. The CMUT device has a size of about 1 to 10 cm.

At least one kind of metal selected from Al, Cr, Ti, Au, PT, Cu, Ag, W, Mo, Ta, Ni or an alloy selected from AlSi, AlCu, AlTi, MoW, AlCr may be used for the upper electrode used in the present invention. The upper electrode may be provided at at least one location on the upper surface, back surface, or inside of the vibration diaphragm. In addition, a configuration may be employed in which, when the vibration diaphragm is formed of a conductor or a semiconductor, the vibration diaphragm serves as the upper electrode. The lower electrode may use a metal similar to that of the upper electrode. When the substrate is made of a semiconductor such as silicon, the substrate may also serve as the lower electrode.

In FIG. 3, all the upper electrodes 502 are electrically connected to one another in the electromechanical transducer device 101, and the control signal generation unit 104 is connected to the upper electrodes 502. The DC voltage applying unit 105 applies a predetermined DC voltage uniformly to the upper electrodes 502 so as to make a predetermined potential difference be generated between the lower electrodes 505 and the upper electrodes 502. In each cell, when an acoustic wave is input to the vibration diaphragm 501, the vibration diaphragm 501 vibrates in accordance with the intensity of the acoustic wave. In the lower electrode 505, electrostatic induction is generated owing to the vibration of the vibration diaphragm 501, whereby a minute current is generated. By converting the current to a voltage using the current-to-voltage conversion unit 102, which is connected to the lower electrode 505 of each cell, an acoustic wave signal to be received can be obtained as a voltage signal for each cell. In the present invention, an electrode connected to the current-to-voltage conversion unit 102 is called a first electrode, and an electrode connected to the DC voltage applying unit 105 is called a second electrode. That is, in FIG. 3, the lower electrode 505 is the first electrode, and the upper electrode 502 is the second electrode. However, the upper electrode 502 may be made to be the first electrode by being connected to the current-to-voltage conversion unit 102, and the lower electrode 505 may be made to be the second electrode by being connected to the DC voltage applying unit 105.

The principle of increasing the required receiver sensitivity for an acoustic wave in accordance with the attenuation of light will now be described. When the capacitive electromechanical transducer device is to be driven, a predetermined potential difference is applied between the first and second electrodes (lower and upper electrodes), whereby the vibration diaphragm 501 enters a state of being deflected toward the substrate 506 owing to electrostatic attractive force generated between the electrodes. When an acoustic wave is received, the strength of a minute current is inversely proportional to the distance between the electrodes and proportional to the potential difference between the electrodes. Hence, a current generated when the vibration diaphragm 501 receives an acoustic wave changes in accordance with the potential difference between the electrodes. More specifically, as the potential difference between the electrodes is increased, the electrostatic attractive force increases, and the amount of deflection of the vibration diaphragm 501 increases, whereby the distance between the electrodes decreases. For fixed vibration corresponding to the case of receiving a fixed acoustic wave, a generated current increases as the distance between the electrodes decreases. In addition to this, the potential between the electrodes is larger. Hence, the generated current is further increased. On the other hand, as the potential difference between the electrodes is decreased, the electrostatic attractive force decreases, and the deflection of the vibration diaphragm 501 decreases, whereby the distance between the electrodes increases. For fixed vibration corresponding to the case of receiving a fixed acoustic wave, a generated current decreases as the distance between the electrodes increases. In addition to this, the potential between the electrodes is smaller. Hence, the generated current is further decreased.

The present embodiment has a configuration in which the control signal 207 generated by the control signal generation unit 104 is output to the DC voltage applying unit 105. The DC voltage applying unit 105 makes a DC voltage applied to the upper electrode 502 change in accordance with the input control signal 207. Thereby, the potential difference between the upper and lower electrodes is made to change, whereby the required receiver sensitivity for an acoustic wave can be changed in accordance with the attenuation of light (an elapsed time from the point in time of irradiation with light). In other words, this means changing a conversion ratio (conversion coefficient) for converting mechanical vibration caused by a received acoustic wave to a current. That is, the control signal generation unit 104, by obtaining this conversion coefficient on the basis of the elapsed time t, generates the control signal 207 corresponding to this conversion coefficient and outputs the control signal 207 to the DC voltage applying unit 105. This alleviates the effect of a decrease in the current output from the electromechanical transducer device 101 caused by the attenuation of light. Thereby, a signal (the voltage 205 output from the current-to-voltage conversion unit 102 in FIG. 1) which is output to an external apparatus for generating image data is eventually adjusted.

Method of Calculating Conversion Coefficient

The conversion coefficient, which is the ratio of conversion from mechanical vibration caused by a received acoustic wave to a current, will now be explained. The method of calculating the conversion coefficient depends on the positional relationship between the direction of irradiation with the light 202 and the electromechanical transducer device 101. First, with reference to FIG. 4, description is made of the case where the acoustic wave receiving surface of the electromechanical transducer device 101 faces in a direction opposite to the radiation direction of the light 202.

Figure 4:
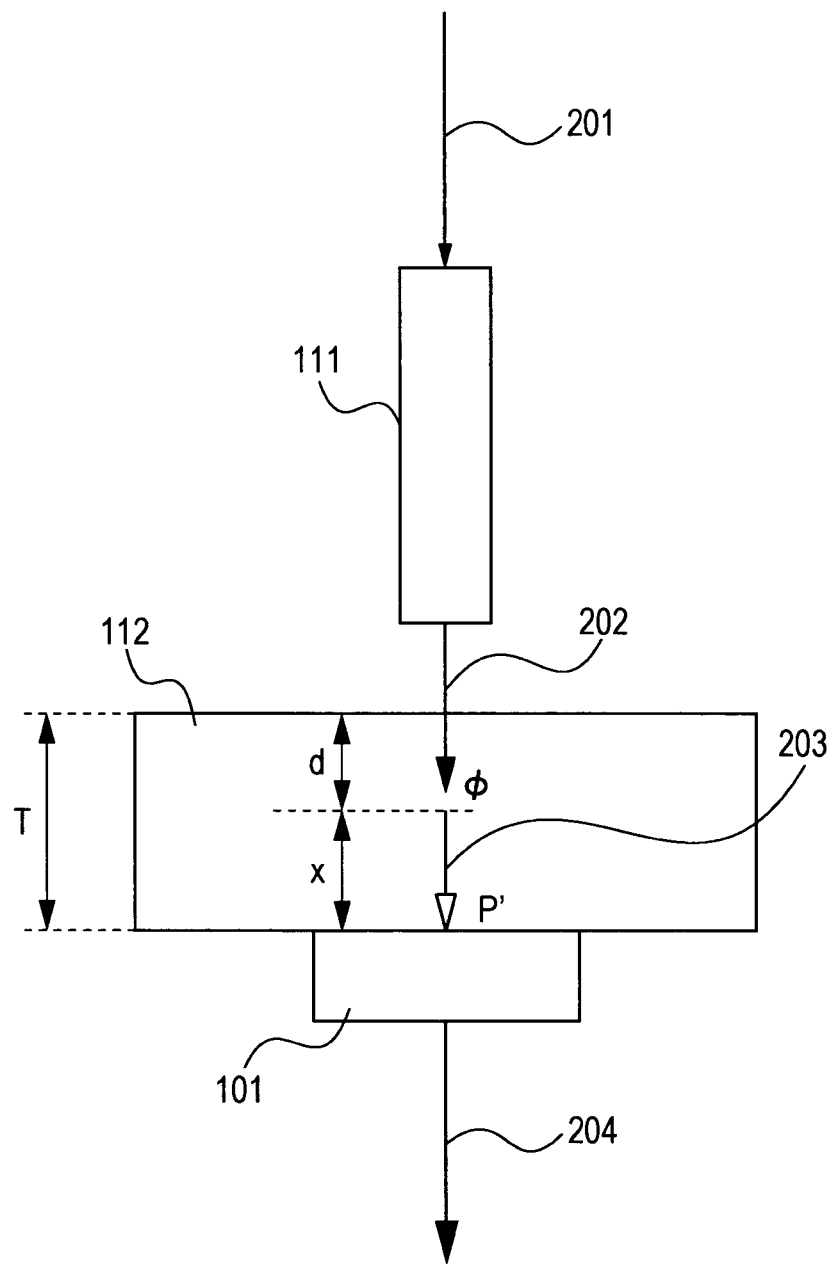
FIG. 4 is a schematic diagram illustrating a method of obtaining a conversion coefficient.

Referring to FIG. 4, the light source 111 radiates the light 202 vertically toward the inspection object 112. The electromechanical transducer device 101 is arranged at a location opposite the light source 111 with the inspection object 112 therebetween. In the description below, it is assumed that the inspection object 112 has a uniform width T, and the electromechanical transducer device 101 is arranged on the inspection object 112 with no gap therebetween. It is also assumed that there is no attenuation of the light 202 between the light source 111 and the inspection object 112.

As the light 202, which has been generated by the light source 111 to irradiate the inspection object 112, passes through the inspection object 112 in the depth direction, the intensity of the light is attenuated exponentially. In other words, within the inspection object 112, portions of the inspection object 112 closer to the light source 111 are irradiated with stronger light and portions of the inspection object 112 farther from the light source 111 are irradiated with weaker light. In the case where there exists an acoustic wave generation source at a location a depth d below the light irradiated surface of the inspection object 112, the intensity φ of light with which the acoustic wave generation source is irradiated is expressed by the following equation.

$$\phi = A \times \exp(-\mu_{eff} \times d) \qquad (1)$$

In Equation (1), A is a coefficient determined by the light intensity, and $\mu_{eff}$ is a coefficient determined by the characteristics of the inspection object 112. Here, since light travels in the inspection object 112 at a very high speed, it can be assumed that the light emitted from the light source 111 arrives anywhere within the inspection object 112 at the same timing as the emission of the light. For given material properties and size of an acoustic wave generation source, the intensity of an acoustic wave generated due to the photoacoustic effect is determined by the intensity of the light with which the acoustic wave generation source is irradiated. In other words, within the inspection object 112, an acoustic wave having a higher intensity is generated at a location nearer to the light source 111, and an acoustic wave having a lower intensity is generated at a location farther from the light source 111. That is, the required receiver sensitivity significantly depends on the locations of acoustic wave generation sources within the inspection object 112.

By letting P be the intensity of an acoustic wave generated when a material having a given structure is irradiated with light having the intensity φ, P is expressed by the following equation.

$$P = B \times \phi = B' \times \exp(-\mu_{eff} \times d) \qquad (2)$$

Here, B and $\mu_{eff}$ are coefficients determined by an acoustic wave generation source. Acoustic waves generated due to the photoacoustic effect propagate through the inspection object 112 in directions toward the electromechanical transducer device 101 and are received by the electromechanical transducer device 101. Since the propagation speed of the acoustic waves within the inspection object 112 are low compared with the speed of light, the electromechanical transducer device 101 receives acoustic waves generated nearer to the electromechanical transducer device 101 (farther from the light source 111) first, and receives acoustic waves generated farther from the electromechanical transducer device 101 (nearer to the light source 111) later.

Here, by letting x be the distance from the electromechanical transducer device 101 to an acoustic wave generation source, and v be the velocity of an acoustic wave propagating through the inspection object 112, a time t from the generation of the acoustic wave until the acoustic wave is received by the electromechanical transducer device 101 is expressed by the following equation.

$$t = x/v \qquad (3)$$

It can be seen from the above description that in the configuration illustrated in FIG. 4, a weak acoustic wave generated by weak light near the electromechanical transducer device 101 is received first, and a strong acoustic wave generated by strong light at a location far from the electromechanical transducer device 101 is received later. Hence, in such a configuration, the present embodiment is characterized in that the conversion coefficient is made large (receiver sensitivity is increased) right after the light source 111 emitted light, and is made smaller (receiver sensitivity is decreased) as time advances.

The depth d at which an acoustic wave generation source is located below the light irradiated surface of the inspection object 112, is expressed by the following equation, using the distance x from the electromechanical transducer device 101 and the width T of the inspection object 112.

$$d = T - x \qquad (4)$$

From Equations (3) and (4), the following equation is obtained.

$$d = T - v \times t \qquad (5)$$

By letting P' be the intensity of an acoustic wave generated by an acoustic wave generation source which is located at the depth d below the light irradiated surface of the inspection object 112, P' can be expressed by the following equation using P (the intensity of an acoustic wave generated when there is no attenuation of light).

$$P' = C \times P/x \qquad (6)$$

C is a coefficient determined by the inspection object 112. From Equations (6), (2), and (5), the following equation is obtained.

[Math. 1]

$$P'(t) = \frac{D}{v \times t} \times \exp\{-\mu_{eff} \times (T - v \times t)\} \qquad (7)$$

D is a coefficient determined by the light intensity of a light source and the photoacoustic effect in the inspection object. Hence by letting the conversion coefficient be K, K is expressed by the following expression using the elapsed time t.

[Math. 2]

$$K(t) = 1/P'(t) = \frac{v \times t}{D \times \exp\{-\mu_{eff} \times (T - v \times t)\}} \qquad (8)$$

Hence, in the case where the acoustic wave receiving surface of the electromechanical transducer device 101 faces in a direction opposite to the radiation direction of the light 202, as illustrated in FIG. 4, the control signal 207 is generated on the basis of the conversion coefficient expressed by Equation (8).

Figure 5:
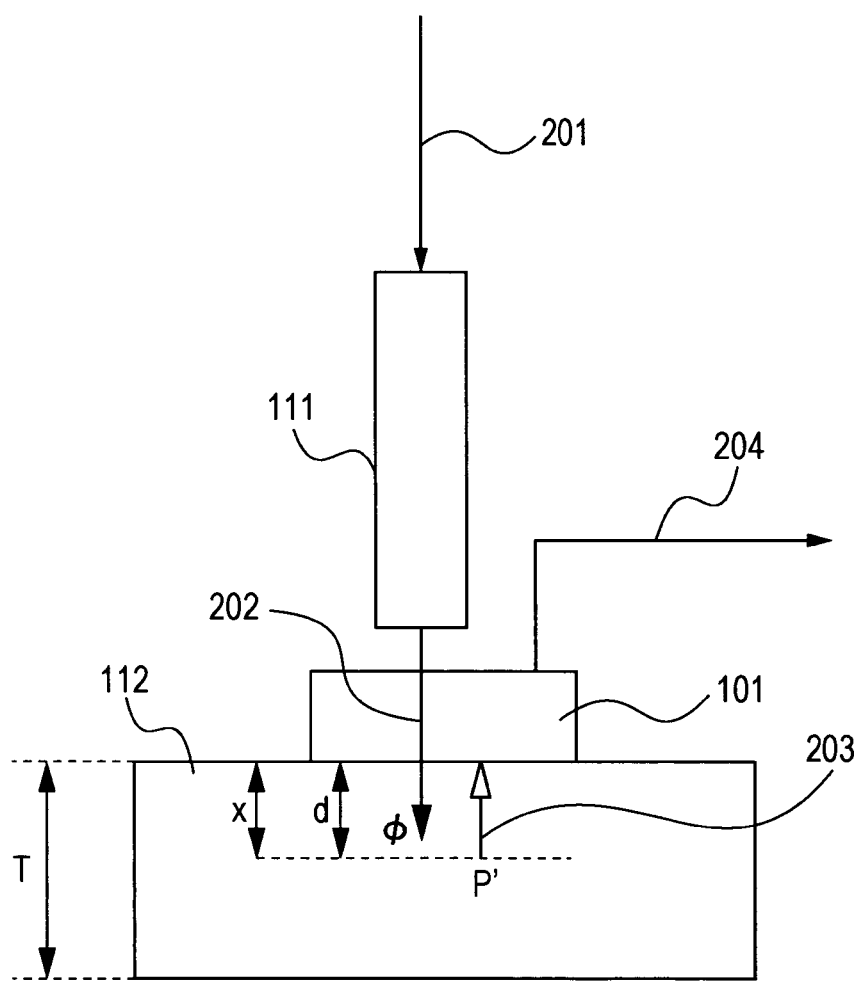
FIG. 5 is a schematic diagram illustrating a method of obtaining a conversion coefficient.

Next, referring to FIG. 5, description is made of the case where the acoustic wave receiving surface of the electromechanical transducer device 101 does not face in a direction opposite to the radiation direction of the light 202, and the light irradiated surface of the inspection object 112 and the acoustic wave receiving surface are arranged on the same side of the inspection object 112.

In FIG. 5, the inspection object 112 is irradiated with the light 202 at a predetermined angle or with the light 202 guided through an optical waveguide provided within the electromechanical transducer device 101, and therefore the light irradiated surface and the acoustic wave receiving surface are arranged on the same side of the inspection object 112. In such a configuration, a strong acoustic wave generated by strong light near the electromechanical transducer device 101 is received first, and a weak acoustic wave generated by weak light at a location far from the electromechanical transducer device 101 is received later. Hence, in such a configuration, the present embodiment is characterized in that the conversion coefficient is made small (receiver sensitivity is decreased) right after the light source 111 emits light, and is made larger (receiver sensitivity is increased) as time advances.

Since the electromechanical transducer device 101 and the light source 111 are arranged on the same side of the inspection object, the depth d from the light irradiated surface of the inspection object 112 to an acoustic wave generation source can be made to be the same as the distance x from the acoustic wave generation source to the electromechanical transducer device 101.

$$d = x \quad (9)$$

Equations (3) and (6) can be rewritten as follows using Equation (9).

$$t = d/v \quad (3')$$

$$P' = C \times P/d \quad (6')$$

Using Equations (2), (3'), and (6'), the intensity P' of an acoustic wave generated by an acoustic wave generation source which is located at the depth d below the light irradiated surface of the inspection object 112 can be expressed by the following equation.

[Math. 3]

$$P'(t) = \frac{D}{v \times t} \times \exp(-\mu_{eff} \times v \times t) \quad (10)$$

In other words, the conversion coefficient K is expressed by the following expression using the elapsed time t.

[Math. 4]

$$K(t) = 1/P'(t) = \frac{v \times t}{D \times \exp(-\mu_{eff} \times v \times t)} \quad (11)$$

Hence, in the case where the light irradiated surface of the inspection object and the acoustic wave receiving surface are provided on the same side of the inspection object, as illustrated in FIG. 5, the control signal 207 can be generated on the basis of the conversion coefficient K expressed by Equation (11).

Further, the conversion coefficient can be also obtained in the case (not shown) where both sides of the inspection object are irradiated with the light 202. In this case, K is expressed by the following Equation (12)

[Math. 5]

$$K(t) = \frac{v \times t}{D1 \times \exp\{-\mu_{eff} \times (T - v \times t)\} + D2 \times \exp(-\mu_{eff} \times v \times t)} \quad (12)$$

D1 and D2 are coefficients determined by the intensity of the light source and the photoacoustic effect in the inspection object.

As described above, even when the arrangement of the surface of the inspection object 112 irradiated with the light 202 and the electromechanical transducer device 101 is changed, the control signal generation unit 104 can obtain the conversion coefficient (conversion ratio for converting mechanical vibration caused by a received acoustic wave to a current, in the present embodiment) on the basis of the elapsed time t from the point in time of the irradiation of the inspection object 112 with light. Then the control signal 207 corresponding to this conversion ratio is generated and output to the DC voltage applying unit 105. In accordance with the input control signal 207, the DC voltage applying unit 105 changes a DC voltage to be applied to the upper electrode 502. Thereby, the potential difference between the upper and lower electrodes is changed, and the required sensitivity for receiving an acoustic wave can be changed in accordance the attenuation of light (elapsed time from the point in time of irradiation with light). This eventually alleviates the effect of a decrease in the signal (the voltage 205 output from the current-to-voltage conversion unit 102 in FIG. 1) which is output to an external apparatus for generating image data.

Obtaining Elapsed Time Information

Figure 6:
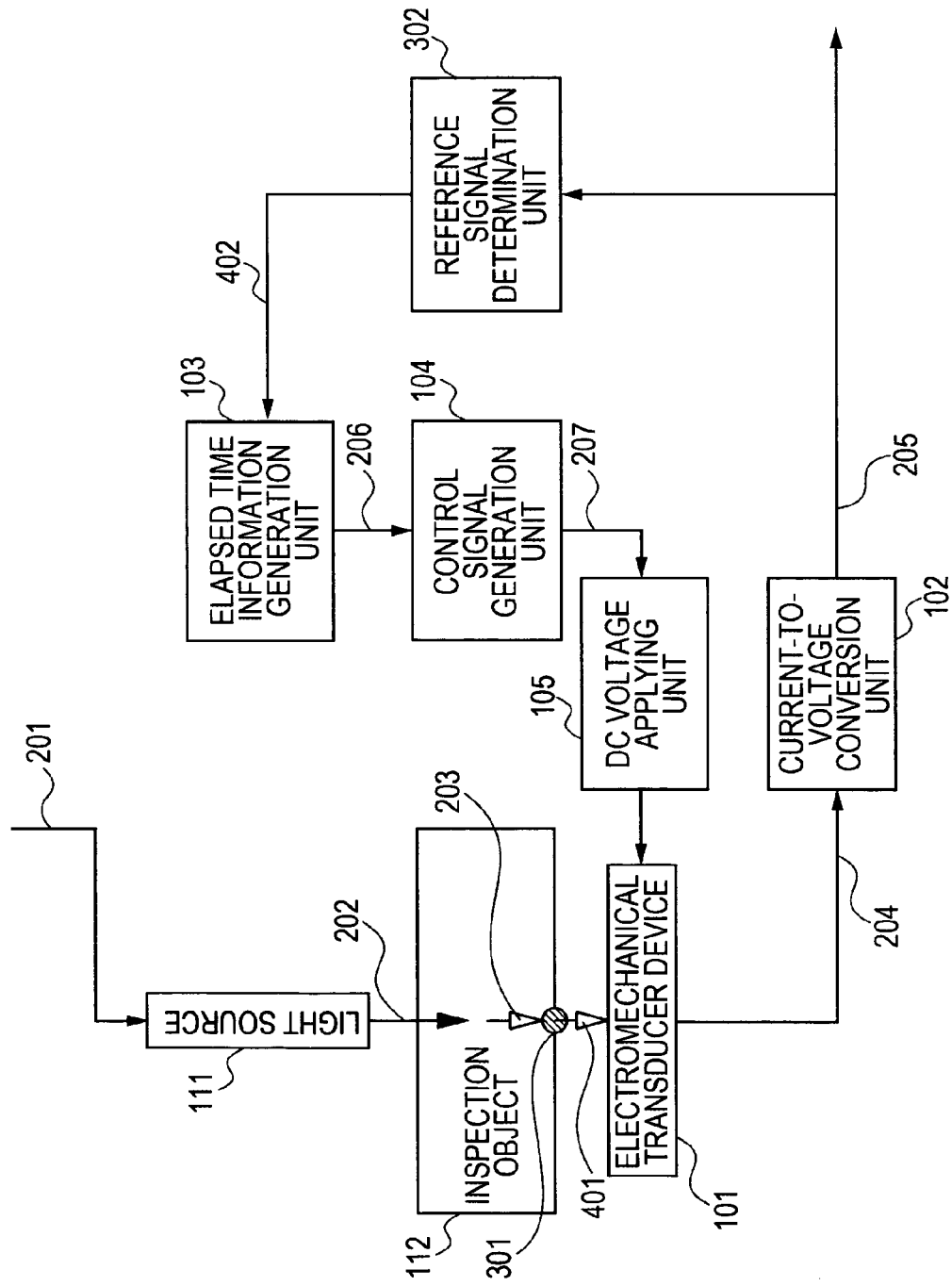
FIG. 6 is a schematic diagram illustrating a measurement system where a reference signal generator is provided.

In the above description, as illustrated in FIG. 1, the elapsed time information generation unit 103 obtains the elapsed time information 206 on the basis of the ON signal (with the center of the pulse width as a reference) that is included in the light emission instruction signal 201 which is a signal for instructing a light source to generate light. However, as illustrated in FIG. 6, by providing a reference signal generator 301 that makes a desirable acoustic wave 401 be generated by the light 202, between the electromechanical transducer device 101 and the inspection object 112, the elapsed time information 206 may be obtained on the basis of the time at which the acoustic wave 401 is received by the electromechanical transducer device 101. In other words, a reference signal 402 for generating the elapsed time information 206 is generated on the basis of the acoustic wave 401 generated by the reference signal generator 301.

In FIG. 6, the reference signal generator 301 is arranged between the electromechanical transducer device 101 and the inspection object 112. More specifically, the reference signal generator 301 may be provided in the vicinity of the surface of the inspection object 112 on the side where the electromechanical transducer device 101 is provided, for example, on the surface of the inspection object 112 or on a plate for keeping part of the inspection object 112 in a predetermined shape. The acoustic wave 401 generated by the reference signal generator 301 arrives at the electromechanical transducer device 101 prior to an acoustic wave 203 generated in the inspection object 112. A reference signal determination unit 302 determines that the acoustic wave 401 generated by the reference signal generator 301 has arrived at the electromechanical transducer device 101, and outputs a reference signal 402 to the elapsed time information generation unit 103. The elapsed time information generation unit 103 generates the elapsed time information 206 on the basis of the reference signal 402.

Here, determination performed by the reference signal determination unit 302 is described. First it is assumed that a sufficient period of time has elapsed after the light source 111 previously emitted light, and all the acoustic waves 203 generated in the inspection object 112 have arrived at the electromechanical transducer device 101. When the light emission instruction signal 201 is input to the light source 111, the light 202 is output with a small delay. This is because it takes some time for the light source 111 to generate the light 202 in response to the light emission instruction signal 201. Since the speed of light is very fast, it is considered that the reference signal generator 301 and the inspection object 112 are irradiated with the output light 202 instantaneously.

Acoustic waves generated by the light 202 are received by the electromechanical transducer device 101 such that an acoustic wave generated at a location closer to the electromechanical transducer device 101 is received earlier. The DC voltage applying unit 105 includes a switch for switching between a receiving state and a non-receiving state for an acoustic wave. When the acoustic wave 401 generated by the reference signal generator 301 has been received, the switch is switched to the acoustic wave receiving state and the current 204 in accordance with the acoustic wave 401 is output. After this, the currents 204 corresponding to the received acoustic waves 401 are sequentially output in accordance with the locations of the acoustic wave generation sources. Here, the reference signal determination unit 302 determines that the acoustic wave 401 generated by the reference signal generator 301 has arrived, on the basis of the non-receiving state having been switched to the receiving state, and outputs the reference signal 402. This prevents the DC voltage applying unit 105 from operating abnormally owing to the influence of noise generated by the light source 111, for example.

By using the acoustic wave 401 generated by the reference signal generator 301 as the reference signal 402 for the elapsed time information generation unit 103, delay in light emission performed by the light source 111 or variation in acoustic wave arrival time due to variation in the arrangement of the light source 111, the inspection object 112, and the electromechanical transducer device 101 can be compensated for.

Second Embodiment

Hereinafter, referring to FIGS. 7A and 7B, the second embodiment is described. In the first embodiment, receiver sensitivity is increased by increasing a drive voltage (DC voltage) applied to the electromechanical transducer device 101 in accordance with the attenuation of light, whereby the current 204 which is output from the electromechanical transducer device 101 is increased. In other words, in the first embodiment, the conversion coefficient for converting vibration due to an acoustic wave received by the electromechanical transducer device 101 to a current is changed on the basis of an elapsed time from the irradiation of an inspection object with light. However, in the second embodiment, the sensitivity of the electromechanical transducer device 101 is not changed, and instead, a conversion ratio for the conversion of a current to a voltage performed by the current-to-voltage conversion unit 102 is increased when the current 204 output from the electromechanical transducer device 101 decreases in accordance with the attenuation of light. In other words, in the present embodiment, a conversion coefficient for current-to-voltage conversion is changed using the current-to-voltage conversion unit 102 on the basis of an elapsed time from the irradiation of an inspection object with light. In other points, the present embodiment is the same as the first embodiment.

Figure 7A:
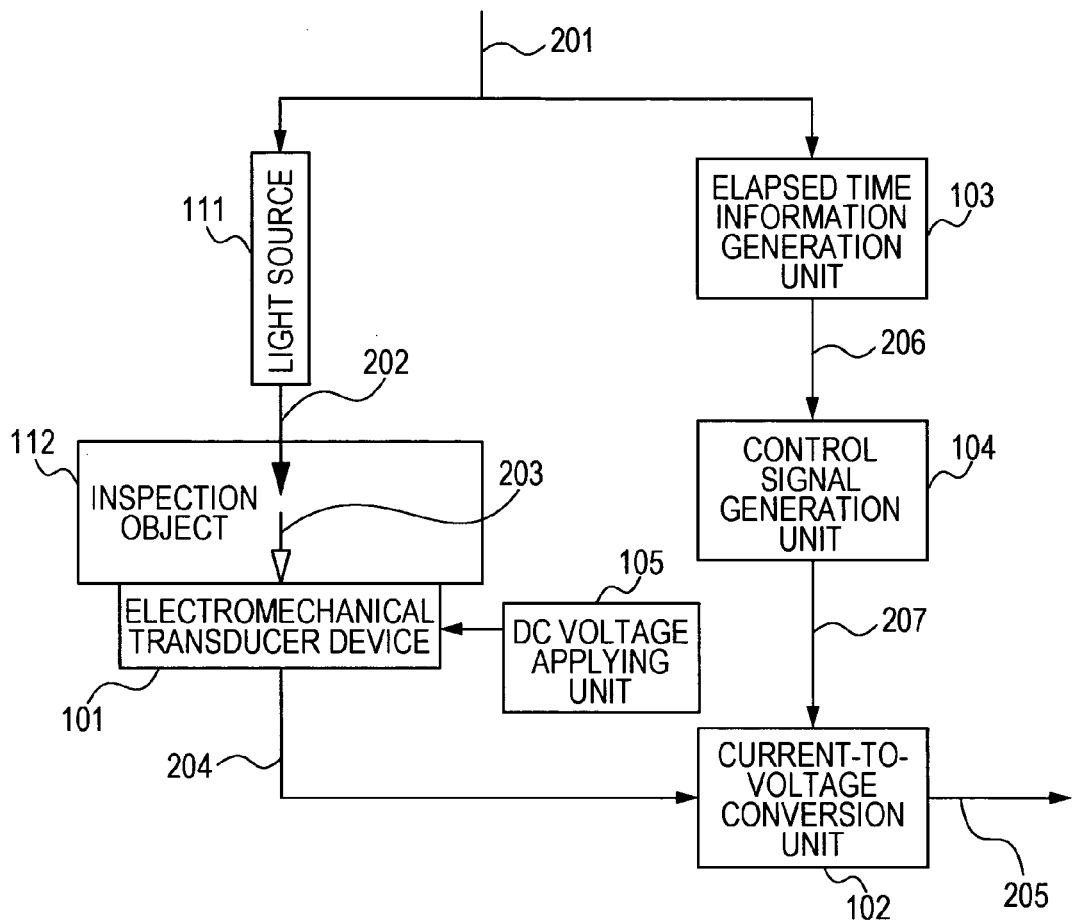
FIGS. 7A and 7B are schematic diagrams illustrating a measurement system according to a second embodiment.

FIG. 7A is a schematic diagram illustrating a measurement system including a control apparatus for the electromechanical transducer device 101 applicable to the present embodiment. Similarly to the first embodiment, the light source 111 generates light 202 (pulsed light), and the inspection object 112 is irradiated with the light 202. An acoustic wave generated in the inspection object 112 as a result of irradiation with the light 202 is received by the electromechanical transducer device 101. The electromechanical transducer device 101 converts vibration due to the received acoustic wave to the current 204, and outputs the current 204 to the current-to-voltage conversion unit 102. The elapsed time information generation unit 103 generates information about a time elapsed from an ON signal (with a point in time corresponding to the center of the pulse width as a reference, for example), included in the light emission instruction signal 201, as the elapsed time information 206, and outputs the elapsed time information 206 to the control signal generation unit 104. Here, in the present embodiment, the control signal 207 generated by the control signal generation unit 104 on the basis of the elapsed time information 206 is output to the current-to-voltage conversion unit 102. The current-to-voltage conversion unit 102 converts the current 204 input from the electromechanical transducer device 101 to the voltage 205 using a conversion ratio (conversion coefficient) based on the control signal 207, and outputs the voltage 205 to an external apparatus (not illustrated) for generation of image data and the like. The conversion coefficient is similar to the conversion coefficient K illustrated in the first embodiment (method of calculating conversion coefficient). That is, the conversion coefficient can be obtained from the relationship between the electromechanical transducer device 101 and the direction of irradiation with light.

Figure 7B:
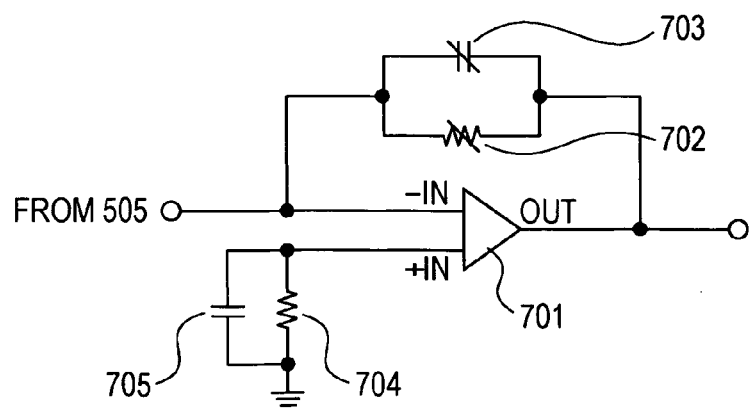

FIG. 7B is a configuration diagram of a transimpedance circuit which is the current-to-voltage conversion unit 102 of the present embodiment. The circuit includes an operational amplifier 701, a variable resistor 702, a variable capacitor 703, a resistor 704, and a capacitor 705.

In FIG. 7B, the operational amplifier 701 is connected to positive and negative power supplies VDD and VSS. First, an operation performed when a change in capacitance has been detected (when an acoustic wave has been received) is described. The inverting input terminal (−IN) is connected to the first electrodes (the lower electrodes 505 in the case of FIG. 3) of the electromechanical transducer device 101. The output terminal (OUT) of the operational amplifier 701 is connected to the inverting terminal (−IN) by the variable resistor 702 and the variable capacitor 703 connected in parallel with each other, whereby the output signal is fed back. The non-inverting terminal (+IN) of the operational amplifier 701 is connected to the ground terminal (GND) by the resistor 704 and the capacitor 705 connected in parallel with each other. The voltage of the ground terminal (GND) is an intermediate voltage that lies between the voltages of the positive power supply VDD and negative power supply VSS.

In the present embodiment, the conversion ratio for current-to-voltage conversion performed by the current-to-voltage conversion unit 102 can be changed by changing the values of the variable resistor 702 and the variable capacitor 703, on the basis of the input control signal 207. Hence, the control signal 207 generated on the basis of the conversion coefficient can be reflected in the electric circuit at a speed sufficiently higher than the speed at which sound pressure changes owing to the attenuation of light.

Similarly to the first embodiment, an elapsed time from irradiation with light may be obtained from the light emission instruction signal 201, or by providing the reference signal generator 301, information about an elapsed time from the time at which an acoustic wave from the reference signal generator 301 was received may be obtained.

Unlike the present invention, a method may be considered in which the gain adjustment is performed by an preamplifier (variable gain amplifier: VGA) provided prior to an AD converter in an external apparatus (not illustrated), to which the voltage obtained by the current-to-voltage conversion unit 102 is output. However, an acoustic wave generated by the photoacoustic effect has a wide frequency band, and the output voltage range is wide. Accordingly, gain adjustment that exceeds the maximum gain (amplification factor) of the preamplifier may be required. Hence, by employing at least one of the method described in the first embodiment, i.e., increasing the current 204 output from the electromechanical transducer device 101 and the method described in the second embodiment, i.e., increasing the conversion ratio for current-to-voltage conversion performed by the current-to-voltage conversion unit 102, a preamplifier without a gain adjustment capability or a preamplifier having a small-range gain adjustment capability can be used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-262068, filed Nov. 17, 2009, which is hereby incorporated by reference herein in its entirety.

REFERENCE SIGNS LIST

101 electromechanical transducer device
102 current-to-voltage conversion unit
103 elapsed time information generation unit
104 control signal generation unit
105 DC voltage applying unit
111 light source
112 inspection object
201 light emission instruction signal
202 light
203 acoustic wave
204 current
205 voltage
206 elapsed time information
207 control signal
501 vibration diaphragm
502 upper electrode
503 supporting unit
504 gap
505 lower electrode
506 substrate

The invention claimed is:

1. A control apparatus that controls an electromechanical transducer device having an element that includes a first electrode and a second electrode arranged with a gap therebetween, and that outputs a current from the first electrode due to receiving an acoustic wave generated by light with which an inspection object is irradiated in a state where a DC voltage is applied to the second electrode, the control apparatus comprising:
a conversion unit configured to convert the current output from the first electrode to a voltage;
a DC voltage applying unit configured to apply a DC voltage to the second electrode; and
a generation unit configured to generate a control signal which makes at least one of the DC voltage and a conversion ratio for converting the current to the voltage be changed, on the basis of elapsed time information about an elapsed time from a point in time at which the inspection object was irradiated with the light.

2. The control apparatus according to claim 1, wherein the elapsed time information is obtained from a light emitting instruction that instructs a light source to emit the light.

3. The control apparatus according to claim 1, wherein the elapsed time information is obtained from time at which the electromechanical transducer device receives an acoustic wave generated from a reference signal generator provided between the inspection object and the electromechanical transducer device.

4. A control method of controlling an electromechanical transducer device having an element that includes a first electrode and a second electrode arranged with a gap therebetween, and that outputs a current from the first electrode due to receiving an acoustic wave generated as a result of an inspection object being irradiated with light in a state where a DC voltage is applied to the second electrode, the method comprising:
converting the current output from the first electrode to a voltage;
applying a DC voltage to the second electrode; and
generating a control signal which makes at least one of the DC voltage and a conversion ratio for converting the current to the voltage be changed, on the basis of information about an elapsed time from a point in time at which the inspection object was irradiated with the light.

5. A measurement system comprising:
a light source;
an electromechanical transducer device that receives an acoustic wave generated as a result of an inspection object being irradiated with light generated by the light source; and
the control apparatus, according to claim 1, arranged to control the electromechanical transducer device.

6. A control apparatus comprising:
a conversion unit configured to convert a current output from a first electrode of an electromechanical transducer to a voltage, the electromechanical transducer having the first electrode and a second electrode arranged with a gap therebetween and outputting the current from the first electrode due to receiving an acoustic wave generated by light with which an inspection object is irradiated;
an applying unit configured to apply a potential difference between the first electrode and the second electrode; and
a generation unit configured to generate a control signal which makes at least one of the potential difference and a conversion ratio for converting the current to the voltage be changed, on the basis of information about an elapsed time from time at which the inspection object was irradiated with the light.

7. The control apparatus according to claim 6, wherein the information is obtained from a light emitting instruction that instructs a light source to emit the light.

8. The control apparatus according to claim 6, wherein the information is obtained from time at which the electromechanical transducer receives an acoustic wave generated from a reference signal generator provided between the inspection object and the electromechanical transducer.

9. The control apparatus according to claim 6, wherein the generation unit generates the control signal which makes the potential difference be changed, and wherein the applying unit changes the potential difference based on the control signal.

10. The control apparatus according to claim 6, wherein the generation unit generates the control signal which makes the potential difference be changed, and wherein the applying unit decreases the potential difference as the elapsed time increases.

11. The control apparatus according to claim 6, wherein the generation unit generates the control signal which makes the potential difference be changed, and wherein the applying unit increases the potential difference as the elapsed time increases.

12. The control apparatus according to claim 6, wherein the generation unit generates the control signal which makes the conversion ratio be changed, and wherein the conversion unit converts the current to the voltage at a conversion ratio based on the control signal.

13. The control apparatus according to claim 6, wherein the generation unit generates the control signal which makes the conversion ratio be changed,
wherein the conversion unit includes a transimpedance circuit including a variable resistor and a variable capacitor, and
wherein the conversion unit changes a value of the variable resistor and a value of the variable capacitor based on the control signal.

14. The control apparatus according to claim 6, wherein the generation unit generates the control signal which makes the potential difference be changed, and wherein the applying unit changes the potential difference corresponding to attenuation of light in the inspection object to be obtained based on the information.

15. The control apparatus according to claim 14, wherein the attenuation of light is obtained based on a distance from a surface irradiated with light on the inspection subject and an amount of light for irradiation.

16. The control apparatus according to claim 14, wherein the applying unit changes the potential difference so as to reduce a decrease in the current that occurs corresponding to the attenuation of light.

17. The control apparatus according to claim 6, wherein the generation unit generates the control signal which makes the conversion ratio be changed, and wherein the conversion unit changes the conversion ratio corresponding to attenuation of light in the inspection subject to be obtained based on the information.

18. The control apparatus according to claim 17, wherein the attenuation of light is obtained based on a distance from a surface irradiated with light on the inspection subject and an amount of light for irradiation.

19. The control apparatus according to claim 17, wherein the generation unit changes the potential difference so as to reduce a decrease in the current that occurs corresponding to the attenuation of light.

20. A measurement system comprising:
a light source;
an electromechanical transducer that receives an acoustic wave generated as a result of an inspection object being irradiated with light generated by the light source; and
the control apparatus according to claim 6, arranged to control the electromechanical transducer.

21. A control method of controlling an electromechanical transducer having a first electrode and a second electrode arranged with a gap therebetween, and outputting a current from the first electrode due to receiving an acoustic wave generated as a result of an inspection object being irradiated with light, the method comprising:
converting the current output from the first electrode to a voltage;
applying a potential difference between the first electrode and the second electrode; and
generating a control signal which makes at least one of the potential difference and a conversion ratio for converting the current to the voltage be changed, on the basis of information about an elapsed time from time at which the inspection object was irradiated with the light.

* * * * *